United States Patent
Chu et al.

(10) Patent No.: US 8,401,612 B1
(45) Date of Patent: Mar. 19, 2013

(54) MAGNETIC RESONANCE IMAGING SYSTEM AND METHOD FOR DETECTING CHIARI MALFORMATIONS

(75) Inventors: Ki-Cheung Chu, Central Islip, NY (US); Raymond V. Damadian, Woodbury, NY (US); Daniel Culver, East Islip, NY (US)

(73) Assignee: Fonar Corporation, Melville, NY (US)

( * ) Notice: Subject to any disclaimer, the term of this patent is extended or adjusted under 35 U.S.C. 154(b) by 813 days.

(21) Appl. No.: 11/900,656

(22) Filed: Sep. 11, 2007

Related U.S. Application Data (60) Provisional application No. 60/843,955, filed on Sep. 11, 2006.

(51) Int. Cl.
*A61B 5/05* (2006.01)

(52) U.S. Cl. ............ 600/410; 600/411; 600/415; 5/601; 5/607

(58) Field of Classification Search ............... 5/601, 607; 600/410, 411, 415; 324/300, 319
See application file for complete search history.

(56) References Cited

U.S. PATENT DOCUMENTS

| | | |
|---|---|---|
| 4,411,270 A | 10/1983 | Damadian |
| 4,534,358 A | 8/1985 | Young |
| 4,629,989 A | 12/1986 | Riehl et al. |
| 4,770,182 A | 9/1988 | Damadian et al. |
| 4,829,252 A | 5/1989 | Kaufman |
| 4,924,198 A | 5/1990 | Laskaris |
| 4,968,937 A | 11/1990 | Akgun et al. |
| 4,985,678 A | 1/1991 | Gangarosa et al. |
| 5,008,624 A | 4/1991 | Yoshida et al. |
| 5,042,487 A | 8/1991 | Marquardt |
| 5,065,761 A | 11/1991 | Pell |
| 5,153,546 A | 10/1992 | Laskaris |
| 5,162,768 A | 11/1992 | McDougall et al. |
| 5,197,474 A | 3/1993 | Englund et al. |
| 5,305,749 A | 4/1994 | Li et al. |
| 5,315,248 A | 5/1994 | Yamaguchi et al. |
| 5,349,956 A | 9/1994 | Bonutti |
| 5,349,959 A | 9/1994 | Wiener et al. |
| 5,436,607 A | 7/1995 | Chari et al. |
| 5,515,863 A | 5/1996 | Damadian |
| 5,565,834 A | 10/1996 | Hanley et al. |
| 5,592,090 A | 1/1997 | Pissanetzky |
| 5,606,970 A | 3/1997 | Damadian |
| 5,735,278 A | 4/1998 | Hoult et al. |
| 5,779,637 A | 7/1998 | Palkovich et al. |
| 5,810,727 A | 9/1998 | Groen et al. |
| 5,993,398 A * | 11/1999 | Alperin ........................ 600/561 |
| 5,997,883 A | 12/1999 | Epstein et al. |
| 6,009,341 A | 12/1999 | Edelman |
| 6,011,396 A | 1/2000 | Eckels et al. |

(Continued)

OTHER PUBLICATIONS

Alperin et al. MRI study of cerebral blood flow and CSF flow dynamics in an upright posture: the effect of posture on the intracranial compliance and pressure. Acta Neurochirurgica Supplement. vol. 95. pp. 177-181. Sep. 19, 2005.*

(Continued)

*Primary Examiner* — Parikha Mehta
(74) *Attorney, Agent, or Firm* — Lerner, David, Littenberg, Krumholz & Mentlik, LLP (57) ABSTRACT

A method for detecting Chiari malformations. The method generally comprises positioning a patient in an upright orientation in a patient-receiving space of a magnetic resonance imaging apparatus and acquiring images of the patient's cerebellum and brainstem in the upright orientation. The method further comprises positioning the patient in a recumbent orientation in the patient-receiving space of the magnetic resonance imaging apparatus and acquiring images of the patient's cerebellum and brainstem in the recumbent orientation.

16 Claims, 9 Drawing Sheets

U.S. PATENT DOCUMENTS

| | | | |
|---|---|---|---|
| 6,023,165 | A | 2/2000 | Damadian et al. |
| 6,122,540 | A | 9/2000 | Katzberg et al. |
| 6,245,027 | B1* | 6/2001 | Alperin .................. 600/561 |
| 6,411,837 | B1 | 6/2002 | Fischer |
| 6,414,490 | B1* | 7/2002 | Damadian et al. ........... 324/319 |
| 6,677,753 | B1 | 1/2004 | Danby et al. |
| 7,102,353 | B1* | 9/2006 | Damadian ................. 324/318 |
| 7,123,008 | B1* | 10/2006 | Damadian et al. ........... 324/309 |
| 7,375,521 | B1* | 5/2008 | Damadian et al. ........... 324/307 |
| 7,378,846 | B1* | 5/2008 | Damadian ................. 324/307 |
| 7,680,525 | B1* | 3/2010 | Damadian et al. ........... 600/415 |
| 7,697,971 | B1* | 4/2010 | Green et al. ............... 600/415 |
| 2004/0138553 | A1* | 7/2004 | Damadian ................. 600/410 |

OTHER PUBLICATIONS

Hoffman et al. Phase-contrast MR Imaging of the Cervical CSF and Spinal Cord: Volumetric Motion Analysis in Patients with Chiari I Malformation. American Journal of Neuroradiology. 21:151-158. Jan. 2000.*

Spinos et al. MR Evaluation of Chiari I Malformations at 0.15T. American Journal of Neuroradiology. 144:1143-1148. Jun. 1985.*

U.S. Appl. No. 10/867,044 with rejections from examiner.

Photographs, "Exhibit at Radiological Society for Northern America," trade show, Dec. 1996.

* cited by examiner

MAGNETIC RESONANCE IMAGING SYSTEM AND METHOD FOR DETECTING CHIARI MALFORMATIONS

CROSS-REFERENCE TO RELATED APPLICATION

This application claims the benefit of the filing date of U.S. Provisional Patent Application No. 60/843,955 filed Sep. 11, 2006, the disclosure of which is hereby incorporated herein by reference.

FIELD OF THE INVENTION

The present invention relates to magnetic resonance imaging systems, apparatus and procedures and, in particular, to apparatus and procedures for detecting Chiari malformations using magnetic resonance imaging.

BACKGROUND OF THE INVENTION

In magnetic resonance imaging, an object to be imaged as, for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the precessing automatic nuclei to rotate or "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. Other conventional MRI imaging instruments use a magnet having a ferromagnetic frame defining a patient-receiving space. Considerable effort has been devoted to design of such magnets in a manner which provides a relatively open patient-receiving space, as opposed to the claustrophobic tubular bore of the conventional solenoidal magnet. However, in these instruments as well, it has been the common practice to provide the patient on a bed which remains horizontal throughout the procedure.

Advancement in magnetic resonance imaging has resulted in imaging apparatus that supports a patient in any position between a vertical position and a horizontal position. As described in greater detail in commonly assigned U.S. Pat. Nos. 6,414,490 and 6,677,753, the disclosures of which are incorporated by reference herein, a magnetic resonance imaging system can be provided with a patient support, such as a table, which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support may include a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the imaging volume of the magnet. Alternatively or additionally, the patient support may be arranged to tilt through a range of orientations between a generally horizontal orientation and a generally vertical orientation.

The position of a patient during magnetic resonance imaging may affect or limit the imaging information obtained. For example, a patient may exhibit a symptom if oriented in an upright or weight bearing position and no symptom if oriented in a recumbent or horizontal position. More specifically, it may be necessary to image a patient in an upright or gravity bearing position to discern a symptom and provide a diagnosis relating to the neck, spine or other areas of the human anatomy.

SUMMARY OF THE INVENTION

In accordance with an aspect of the present invention, the craniospinal junction of a patient is preferably imaged in at least two body postures, the recumbent and the upright position, in an MRI scanner. The images of craniospinal junction in the recumbent and upright positions can be displayed to show the level of crowding in the cranial-spinal junction, which may assist in the diagnosis of Chiari malformations.

In another aspect, the present invention comprises a method for magnetic resonance imaging. The method preferably comprises positioning a patient on a patient-receiving apparatus in an upright orientation in a patient-receiving space of a magnetic resonance imaging apparatus, acquiring magnetic resonance signals of the patient's cranio-spinal tissue in the upright orientation, rotating the patient-receiving apparatus so that the patient is positioned in a recumbent orientation in the patient-receiving space of the magnetic resonance imaging apparatus, and acquiring magnetic resonance signals of the patient's cranio-spinal tissue in the recumbent orientation. The method may further comprise measuring of cerebrospinal fluid flow and/or motion of the spinal cord of the patient in the upright orientation and the recumbent orientation. The method also preferably comprises analyzing the magnetic resonance signals acquired in the upright and recumbent positions to detect positional dependence of the cranio-spinal tissue.

Further in accordance with this aspect of the present invention, the method may comprise processing the measurement of the cerebrospinal fluid flow to produce one or more images of the cerebrospinal flow with respect to the patient's cardiac cycle.

The method may also desirably comprise processing the magnetic resonance signals to produce an image of the head of the patient along the coronal plane in the recumbent and upright positions. The method may also further comprise processing the magnetic resonance signals to produce an image of the head of the patient along the sagittal plane in the recumbent and upright positions. The method may also comprise processing the magnetic resonance signals to produce an image of the head of the patient along the transverse plane in the recumbent and upright positions.

In another aspect, the present invention may also comprise a method comprising operating a magnetic resonance imaging system to acquire magnetic resonance signals from a head of a patient positioned on a patient support in a recumbent position; rotating the patient support to place the patient in an upright position; operating the magnetic resonance imaging system to acquire magnetic resonance signals form the head of the patient in the upright position; and processing the magnetic resonance signals acquired in the upright and recumbent positions to produce an image of a portion of the patient's head in the recumbent and upright position so that the image shows the patient's craniospinal junction.

In accordance with this aspect of the present invention, the step of operating the system to acquire magnetic resonance image signals is triggered based on the cardiac cycle of the patient. The method may also further comprise processing measurements of the cerebrospinal flow to produce an image of the cerebrospinal flow of the patient in the upright and recumbent positions.

In another aspect, the present invention may also comprise a magnetic resonance imaging system. The system may comprise a pair of elements operable to generate a static magnetic field spaced apart along a horizontal axis to form a patient receiving space; a patient support apparatus located within the patient receiving space, the patient support apparatus capable of supporting a patient in a recumbent position and rotating the patient from the recumbent position to an upright position; an image acquisition system for receiving magnetic resonance signals from a portion of the patient's anatomy; an image processing system for producing images of portions of the patient's anatomy based on the received magnetic resonance signals, the image processing system being operable to produce one or more images of a portion of the patient's head in the recumbent and upright position so that show the patient's craniospinal junction.

DESCRIPTION OF THE INVENTION

Chiari malformations are abnormal placements of the cerebellum, which is the part of the brain that controls balance. Typically, the cerebellum and brainstem can be pushed downward into the spinal canal. The resulting crowding of the cranial-spinal junction can block the flow of cerebrospinal fluid ("CSF") (which in addition to providing other functions in the body, is the liquid that surrounds and protects the brain and spinal cord) and can cause a range of symptoms including dizziness, muscle weakness, numbness, vision problems, headache, and problems with balance and coordination. Other conditions sometimes associated with Chiari malformations include hydrocephalus, syringomyelia, and spinal curvature. The number of cases in the United States is estimated to range from 200,000 to 2 million.

In general, in Chiari malformations the cerebellar tonsil descends into the foramen magnum opening at the back of the skull base by more than 5 mm. The degree of tonsillar herniation, however, correlates poorly with the presence and severity of symptoms. Although most malformations are congenital, they usually are not apparent at birth. Rather, they are usually not apparent until a person is in their twenties or thirties. These malformations can also be acquired through head and neck trauma such as whiplashes from car accidents.

There are three primary types of Chiari malformations. The most common is Type I, which may not exhibit symptoms and is often found by accident during an examination for another condition. Type I malformations are estimated to account for 70% of all Chiari malformations. Type II (also called Arnold-Chiari malformation) is usually accompanied by a myelomeningocele-a form of spina bifida that occurs when the spinal canal and backbone do not close before birth, causing the spinal cord to protrude through an opening in the back. This can cause partial or complete paralysis below the spinal opening. Type III is the most serious form of Chiari malformations, and causes severe neurological defects.

Up to now, Chiari malformations have typically been diagnosed by imaging the head and spine of a patient in the horizontal or supine position. In accordance with an aspect of the present invention, we have discovered that by imaging a patient in several positions with varying degrees of body inclination and head orientation, diagnosis of Chiari malformations can be enhanced. These positions may include the upright position (90° from the horizontal, i.e., sitting-up or standing-up) and the Trendelenburg position (negative angles from the horizontal, i.e., inverted positions where the head is lower than the feet). In addition, in these positions, the head can also be tilted forward (flexion) or backward (extension), sideways to the left or right, and rotated towards the back to the left or right.

The current technique of imaging only in the recumbent position for Chiari malformation is not as conclusive as it is for other diseases such as cancer. This is so because Chiari malformations generally stem from the dropping of brain content into the spinal canal and this condition is affected by the direction of gravitational pull relative to the craniospinal geometry. Our pilot study in Chiari malformation has demonstrated this effect.

In accordance with an aspect of the present invention, imaging the patient in different postures, including the upright position, provides diagnostic information unavailable before. Thus, changes in the Chiari conditions can be presented visually when the patient is lying down versus upright, which is the prevalent daily posture. This extra knowledge will enhance the diagnosis and decision of treatment strategies in the care of Chiari patients. Even after more than a century since its discovery, Chiari malformation is still a poorly understood disease with lots of unresolved questions about its pathophysiology and selection of surgical procedures. In one aspect, this invention provides a new method to address these concerns and provides new and unexpected results. Specifically, the following areas will likely benefit from postural information in Chiari malformation.

First, symptoms for Chiari malformations generally exhibit a postural dependence. One of the puzzling questions in Chiari malformation is why some patients are symptomatic while others are asymptomatic. About one-third of individuals with tonsillar herniation are without symptoms. Furthermore, patients often express different types and varying severity of symptoms when lying down, bending forward, sitting up or standing straight. By imaging the patient in different positions, deterministic information on the causative factors of symptoms can be determined.

Second, among the many unanswered questions on the treatment side are indications for surgery, choice of different surgical procedures available, and treatment for asymptomatic patients if any. When a patient is placed in the Trendelenburg position, gravity is expected to pull the tonsillar descent back into the skull, and hence clears the obstruction of the foramen magnum. By imaging in this position, prospective information is non-invasively acquired about the possible outcome of decompression surgery.

In accordance with an aspect of the present invention, the craniospinal junction of a patient is preferably imaged in at least two body postures, the recumbent and the upright position, in an MRI scanner. In each posture, the following scans are carried out:

1. Anatomical

Typically, T1 and T2 weighted magnetic resonance images in the sagittal, coronal, and axial planes are acquired. This allows for the visualization of shifts in cerebral and spinal tissues when the patient is in different postures. In our pilot study, postural changes in the ventricle size, degree of tonsillar herniation, degree of risk herniation in the spine, morphology of the cerebellum and brain stem have been observed. Current imaging being confined to the recumbent position only, is in a sense artificial and does not reflect the realistic anatomical changes experienced by the patients in real life.

2. Dynamical

Cine Phase-contrast MRI with cardiac gating (i.e., triggering the measurements based on the cardiac cycle) is acquired. The measurements are triggered using an ECG measuring device that is connected to the patient and that generates a trigger pulse for each cardiac cycle. That pulse is then provided to the magnetic resonance imaging system to initiate imaging. This yields two types of information:

A. Displacement

By displaying the magnitude of the cine phase-contrast images throughout the cardiac cycle, it shows how the cerebrospinal tissues are moving. In our pilot study, we observed a dramatic increase in the movement of cerebrospinal tissues in some Chiari patients compared to healthy people in whom such movements are unnoticeable. Furthermore, such movements in Chiari patients are highly posture dependent. Measurement of displacement and geometry can be made to quantify these postural changes from the magnitude images. Scarring and adhesion are easily visible, which could be correlated with the absence or presence of symptoms, the types of symptoms, and postural dependence of symptoms.

B. Velocity

By displaying the phase of the cine phase-contrast images throughout the cardiac cycle, it shows the velocity of any moving tissues throughout the cardiac cycle. Particular tissues of interest include the cerebrospinal fluid (CSF) and blood flow in and out of the cranium, as well as the spinal cord. Descent of tonsillar herniation into the cervical spinal canal blocks the flow of CSF and abnormal CSF flow patterns have been associated with the creation of syrinx in Chiari patients. As a result, studying the CSF pulsation waveform and quantifying its flow parameters offer valuable information about the hydrodynamical state of the patient in various postures. Imaging of blood flow is also important since the arterial blood flow from the heart into the cranium is the driving force of CSF pulsations.

Imaging may also be done with the patient oriented in the Tredenlenburg position. In the Trendelenburg position the body is laid flat on the back with the head lower than the pelvis.

Figure 1:
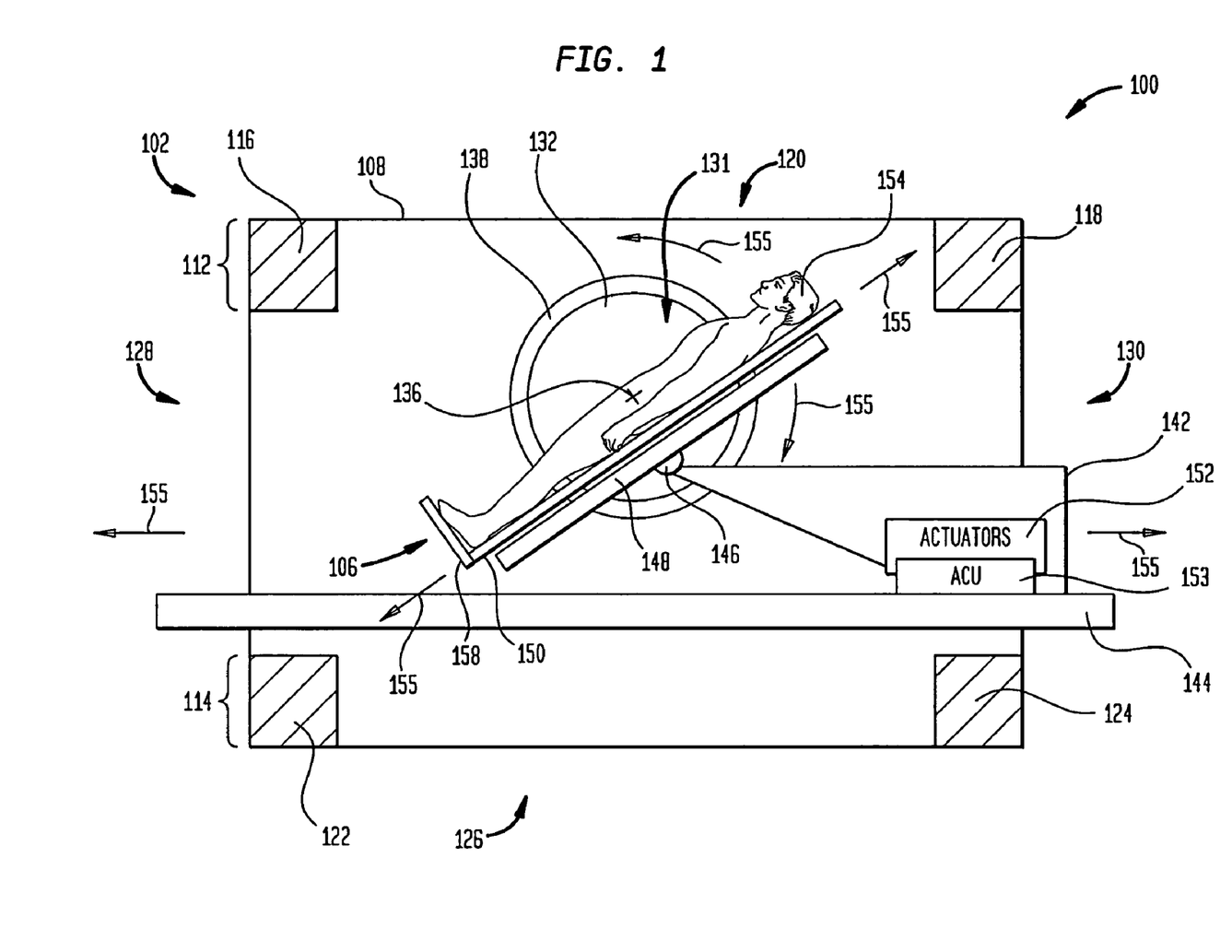
FIG. 1 illustratively depicts a magnetic resonance imaging system in accordance with an aspect of the present invention.

In the preferred embodiment, imaging and the other measurements discussed above may be done using an MRI scanner as shown in FIG. 1. FIG. 1 shows a sectional view of an MRI magnet subsystem 100. MRI magnet subsystem 100 includes a magnet having a ferromagnetic frame 102, a flux generating means as is described in further detail below, and a patient handling system 106. The ferromagnetic frame 102 includes a first side wall 108 and a second side wall. For purposes of clarity, FIG. 1 does not show the second side wall or any of its associated structures. But the second side wall lies in a plane opposite the first side wall 108 on the other side of the patient along with the required associated structures.

The side walls extend vertically. The ferromagnetic frame 102 also includes a top flux return structure 112 and a bottom flux return structure 114. The top flux return structure 112 may include two columns 116 and 118. Between these two columns, a top opening 120 is defined. Similarly, the bottom flux return structure 114 may include two columns 122 and 124 that together define a bottom opening 126. Thus, the side walls and flux return structures 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 of the rectilinear structure defines a front patient opening 128 on one side of the frame 102 and a similar back patient opening 130 on the opposite side of the frame 102. The ferromagnetic frame 102 further includes a first magnetic pole 132 and a second magnetic pole. The first magnetic pole 132 extends from the first side wall 108 towards the second side wall and the second magnetic pole extends from the second side wall towards the first side wall 108. The magnetic poles are generally cylindrical and are coaxial with one another on a common horizontal polar axis 136. Between the magnetic poles is a gap 131, also referred to as the patient-receiving space, of the magnet. The gap or patient-receiving space 131 is accessible by the front patient opening 128, the back patient opening 130, the top opening 120 or the bottom opening 126.

The flux generating means includes a first electromagnetic coil assembly 138 which surrounds the first magnetic pole 132, and a second electromagnet coil assembly, which surrounds the second magnetic pole in a like fashion. These electromagnetic coil assemblies may be either resistive or superconductive.

The patient handling system 106 is capable of three degrees or axes of motion. The patient handling system 106 may be termed an upright patient handling system, although the patient handling system 106 is not limited to standing position applications and may include sitting and other upright positions, as well as the recumbent position. The patient handling system 106 preferably includes a carriage 142 mounted on rails 144. The carriage 142 may move linearly back and forth along the rails 144. The rails 144 typically do not block the bottom open space 126. A patient handling system operative in the manner described herein is disclosed in U.S. application Ser. No. 09/918,369, filed on Jul. 30, 2001, which is entitled "Positioning System For An MRI," the disclosure of which is incorporated by reference herein.

A generally horizontal pivot with an axis 146 is mounted on carriage 142. An elevator frame 148 is mounted to pivot about the axis 146. The carriage 142 is operable to rotate the elevator frame 148 about the pivot axis 146. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement or motion. Specifically, the patient handling system 106 can move a patient 154 in two linear directions and also rotate the patient 154 around an axis. The arrows 155 of FIG. 1 show the three axes of movement possible with the patient handling system 106. Note that often the rails 108 are mounted such that portions of patient 154 may be positioned below the rails through bottom open space 126.

Often, a foot rest 158 may be used in order to support a patient in a standing position. Given the wide variety of positions possible with the patient handling system 108, many other such supports may be implemented, such as chair seats or straps.

The patient handling system 106 incorporates one or more actuators 152 and an actuation control unit 153. Actuators 152 may be conventional electrical, electromechanical, pneumatic, hydraulic or other devices capable of imparting the desired motion to the elements of the patient handling system. For example, the actuators may include elements such as conventional stepper motors or other conventional electric motors linked to the elements of the patient handling system 106. The actuator control unit 153 may incorporate a conventional programmable controller, microprocessor, or computer with appropriate input and output interfaces. As further discussed below, the actuation control unit 153 is linked to a control computer and to the manual controls which regulate the patient handling system. The actuation control unit may be mounted in proximity to the actuators 152 as, for example, on carriage 142. In addition to actuation control, the system also preferably includes processor or computer that control the pulse sequences that cause small gradients in the static magnetic field. As explained above, by using different combinations of gradients, a map of signal characteristics versus location may be displayed.

Figure 2A:
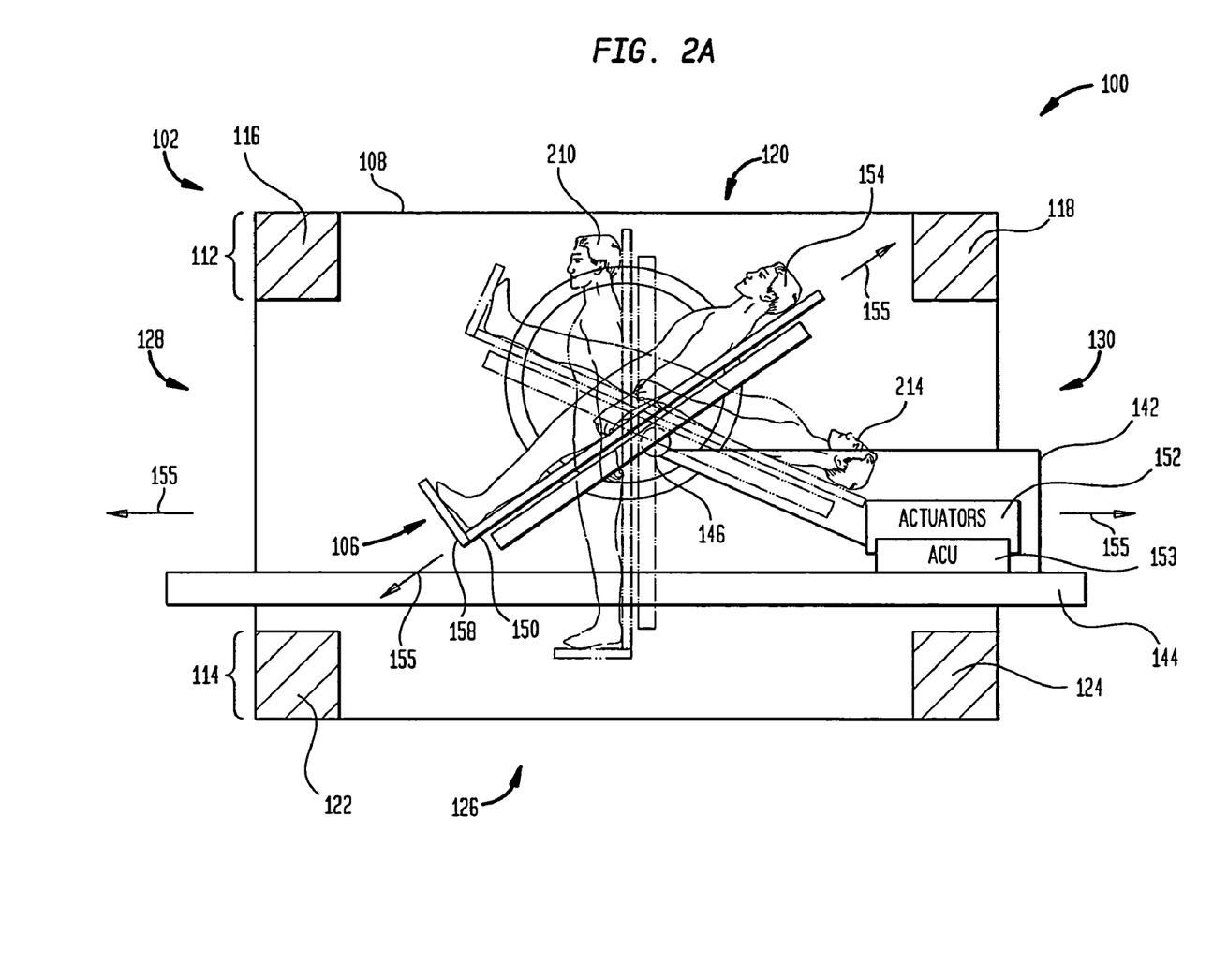
FIG. 2A illustratively depicts the magnetic resonance imaging system of FIG. 1 with a patient oriented in various positions.

As shown in dotted outline in FIG. 2A, patient support 150 may be oriented between a variety positions including the upright position 210 and the Trendelenburg position 214. The patient support may also be oriented in any positions between these two positions, including a horizontal condition in which the patient support 150 is generally horizontal.

As is discussed above, the measurements are triggered using an ECG measuring device that is connected to the patient and that generates a trigger pulse for each cardiac cycle. That pulse is then provided to the magnetic resonance imaging system to initiate imaging. Triggering devices that provide this functionality are commercially available.

The system 100 typically includes a display and other processing elements, e.g., a microprocessor general purpose processor or more generically a computer or workstation, that process the magnetic resonance images for display. Such computers may include a personal computer running the Windows operating system and having software for executing image processing instructions. In other embodiments, the processing element may comprise a workstation, such as for example, a Unix based workstation. Such processing may result in displays of slices along different planes of the human anatomy (coronal, saggital or transversal), as well as along the axial direction. In some embodiments, after image processing the images are displayed on a monitor, e.g., liquid crystal display, television monitor or any other display device. In other embodiments, the processing elements produce signals that can be used by a printer to produce one or more images. Control of the MRI system, including image acquisition and display, may be done as is disclosed in commonly assigned U.S. Pat. No. 6,336,094, which is incorporated by reference herein, or using other techniques.

Figure 2B:
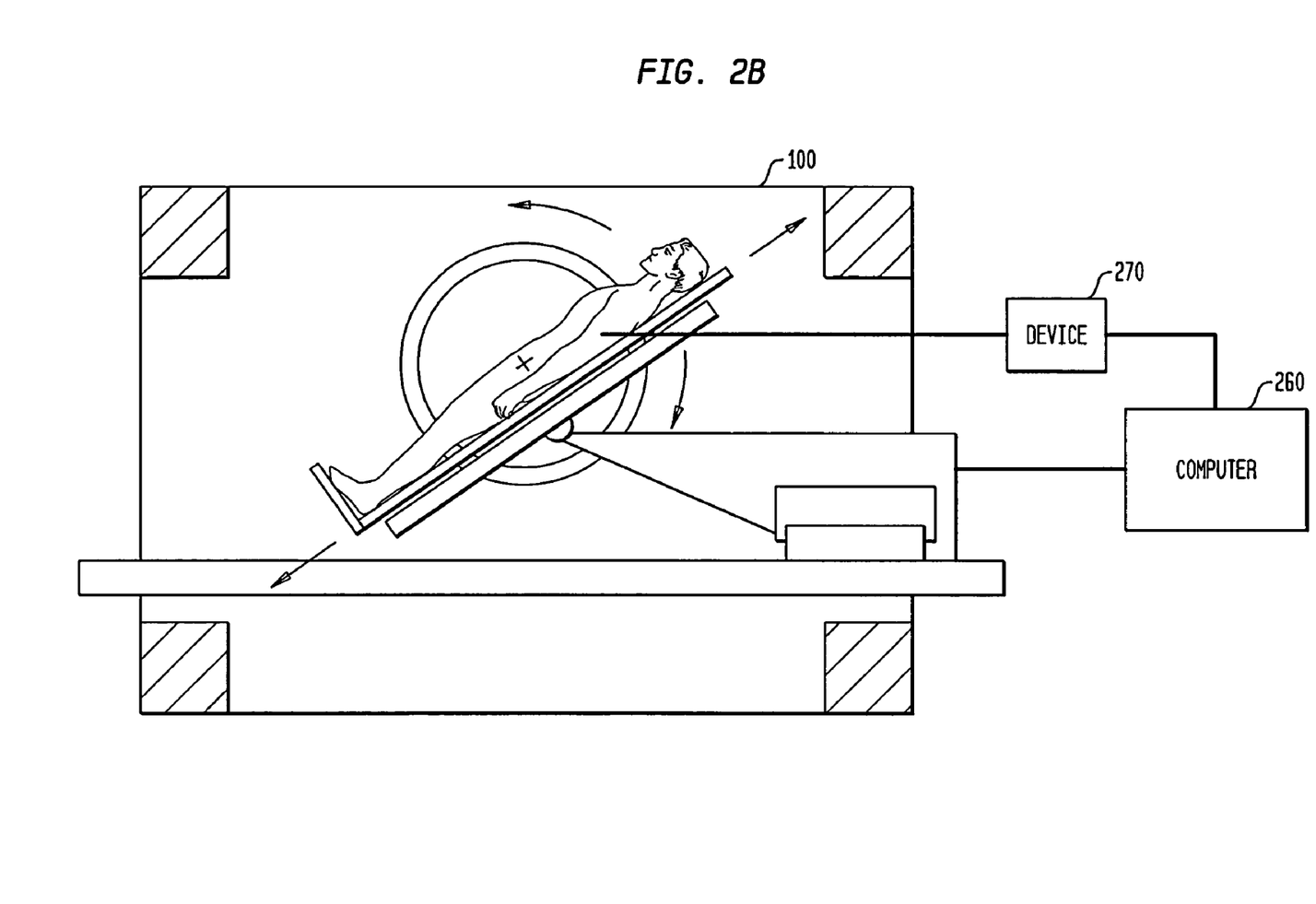
FIG. 2B is a block diagram showing a measurement system in accordance with an aspect of the present invention.

FIG. 2B shows a high level block diagram of the system 100, computer or processor 260 and triggering device 270. As explained above, the triggering device 270 provides a pulse to the computer 260 which initiates image acquisition, as for example and ECG. The triggering device may look at the electrical activity of the heart. Another triggering device that may be used is a pulse oximeter which provides an output pulse based on oxygen content of the blood.

FIGS. 3 through 7 shows images of a patient's anatomical area of interest obtained in accordance with the various aspects of the present invention. In each figure, the image on the left is for the patient in the recumbent position (as is indicated in the image itself by the label R) and the image on the right is for an upright position (as is indicated by the label U). The figures generally show the following.

Figure 3:
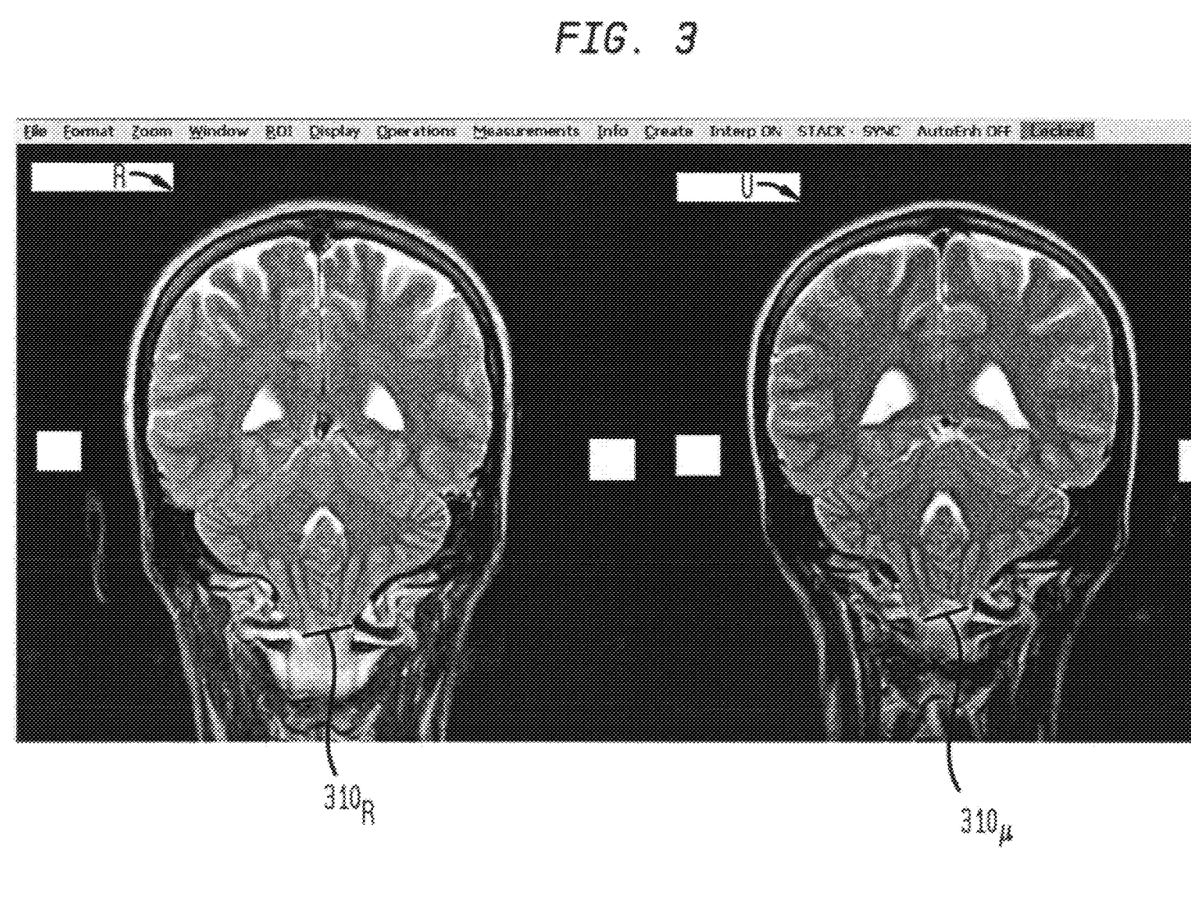
FIG. 3 is an image of a coronal scan of a patient in a recumbent (on the left) and an upright position (on the right).

FIG. 3 shows a coronal T2 weighted MRI scan of a patient's head. This patient is believed to suffer from the Chiari condition. In this image, the patient showed greater amount of asymmetry between left and right tonsillar descent when the patient was upright than recumbent. In other words, it showed that the right cerebellar tonsil dropped more into the spinal canal than the left tonsil in the upright position. This effect is shown by the slope of the lines 310 in the FIG. 3.

Figure 4:
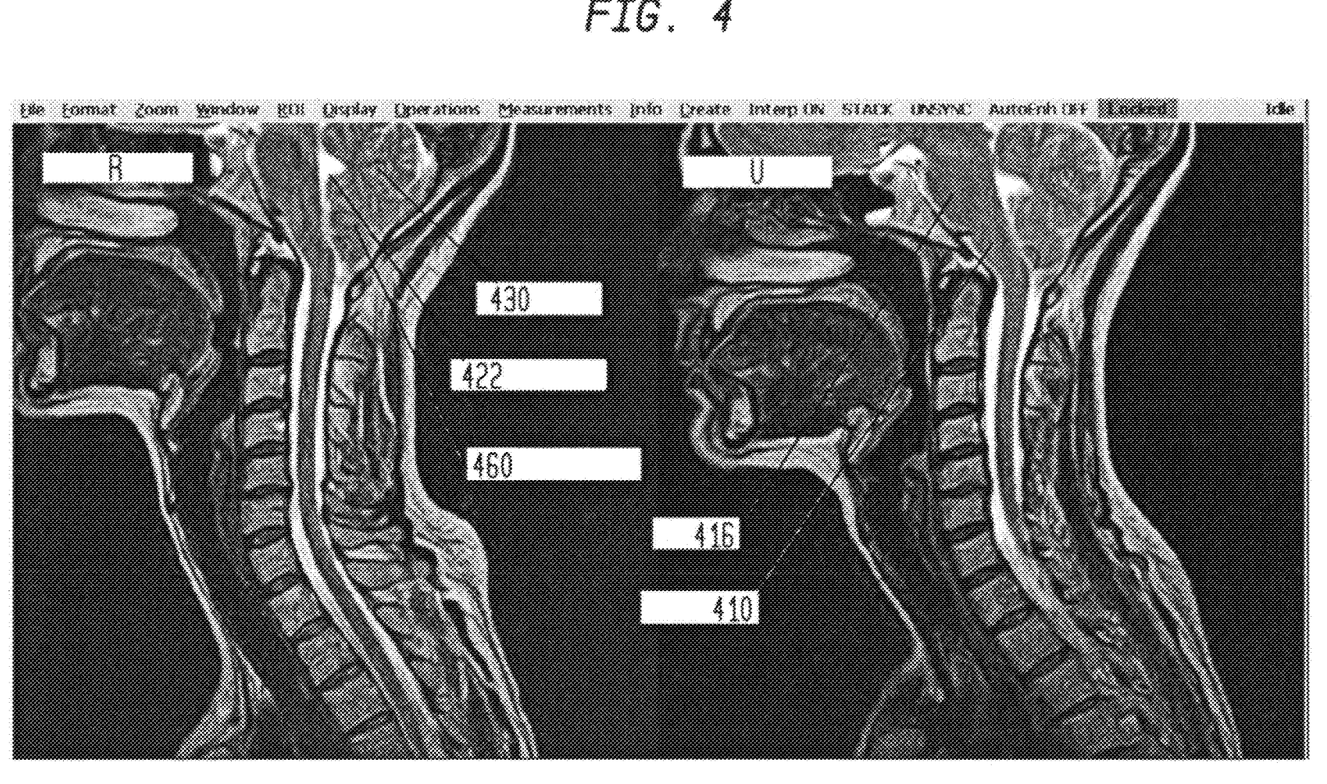
FIG. 4 is an image of a sagittal scan of a patient in a recumbent (on the left) and an upright position (on the right).

FIG. 4 shows a sagittal T2 weighted scan of the patient's head. (Note that the images in FIGS. 3-7 are of the same patient.) This figure shows the brain stem 410 and pons 416 tissue were more bent when the patient was upright U than recumbent R. Also, the shape of the cerebellum 430 was different in the two positions.

Figure 5:
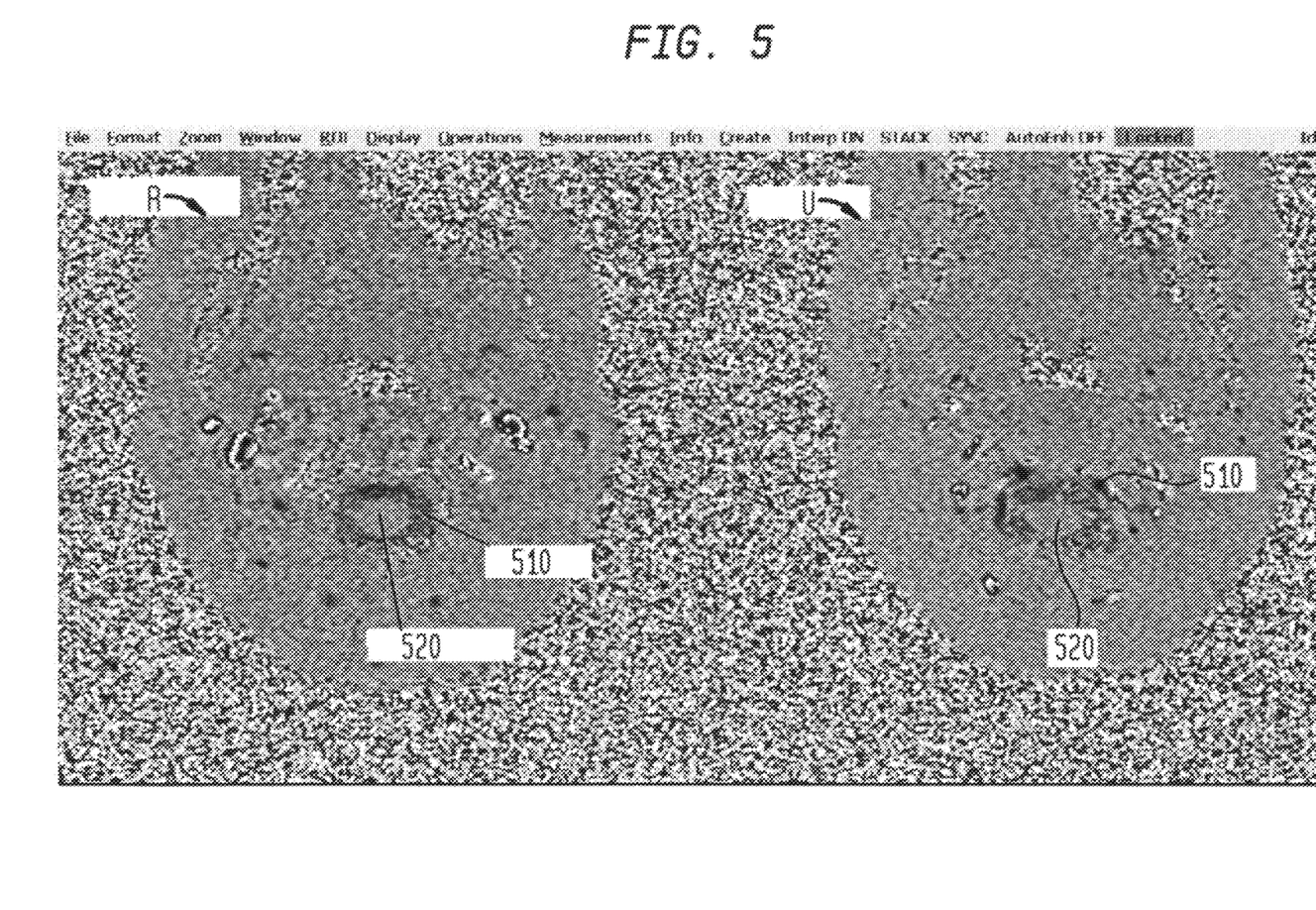
FIG. 5 is an image showing cross-sectional cut across the neck of a patient in a recumbent (on the left) and an upright position (on the right).
Figure 6:
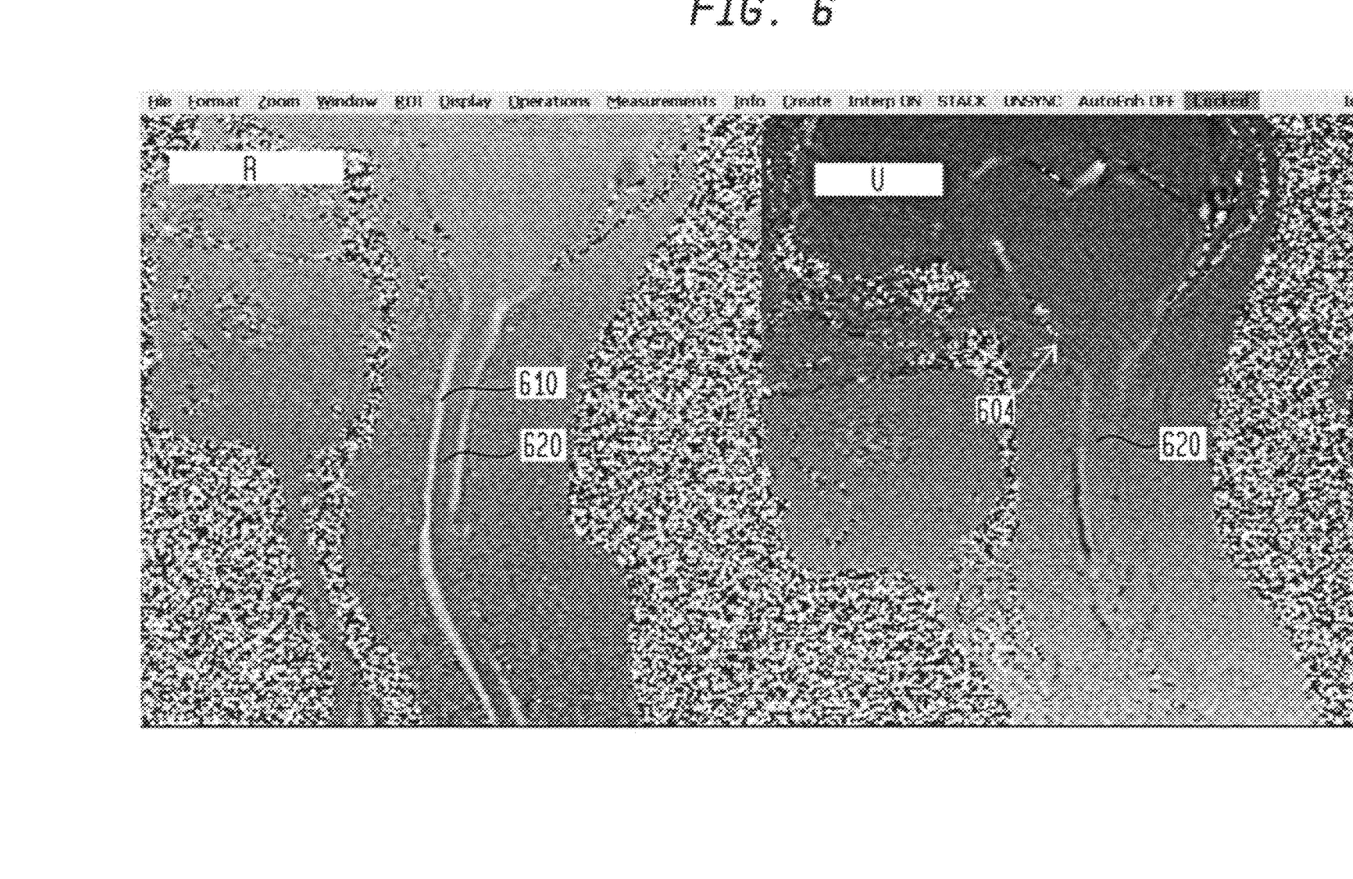
FIG. 6 is an image showing a sagittal cut of a patient in a recumbent (on the left) and an upright position (on the right).

FIGS. 5 and 6, respectively, shows CSF flows along the axial and sagittal planes/direction with the patient in the upright U and recumbent R positions. As can be seen from the figures, the CSF flow 510, 610 is more obstructed (see arrow 604) around the spinal cord 520, 620 in the upright U position than in the recumbent R position. Also note with respect to FIG. 6 the change of CSF flow patency down in the cervical spine, both anterior and posterior to the spinal cord. Those skilled in the art will appreciated that FIGS. 5 and 6 show one frame at an instant of time. However, when multiple frames are collected over time and shown as a moving picture, the difference between CSF flow in the different positions are more clearly discernable. In fact, FIGS. 5 and 6 each comprise one frame from respective 32 frame sequences. These images were used to generate the quantitative flow information exhibited in FIG. 8.

Figure 7:
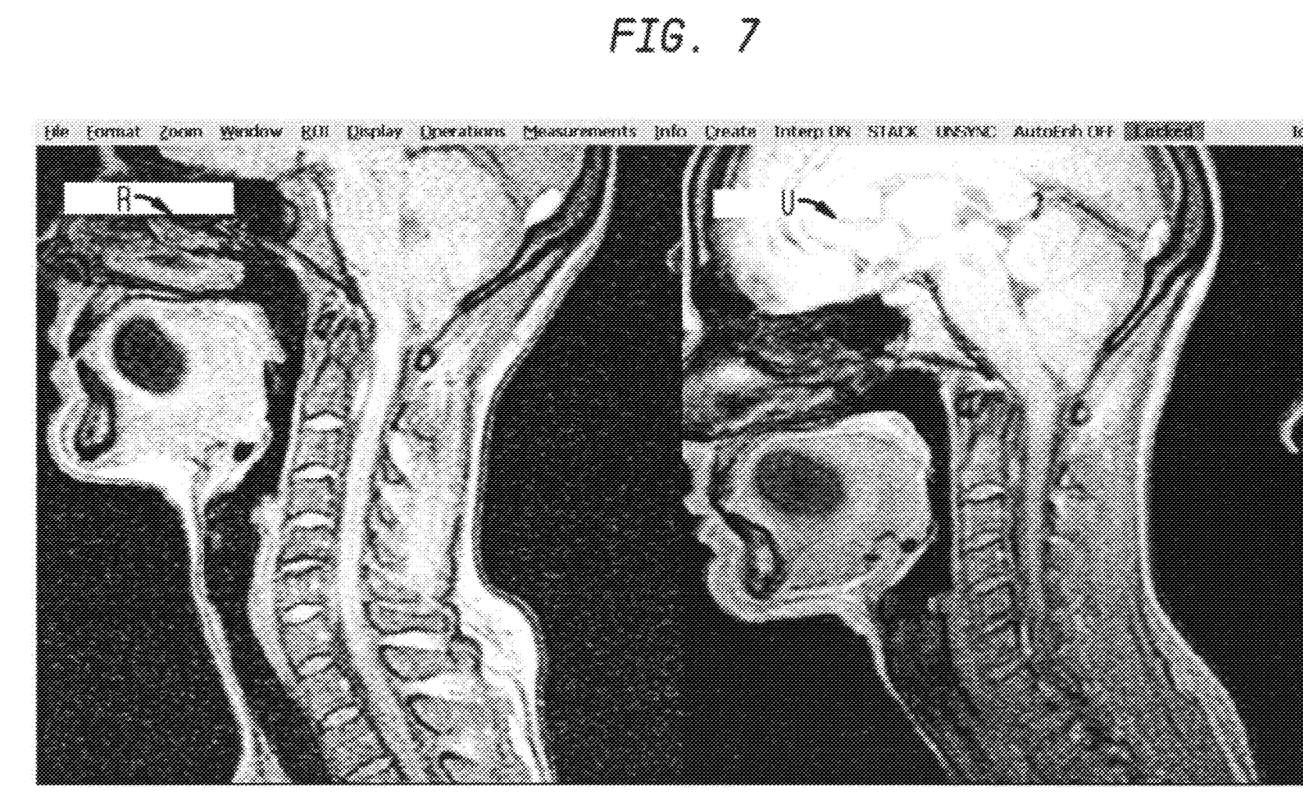
FIG. 7 is an image of a sagittal scan of a patient in a recumbent (on the left) and an upright position (on the right).

FIG. 7 is an image of a saggital scan of the patient in a recumbent R (on the left) and an upright position (U on the right). FIG. 7 is one frame of a multi-frame sequence. It shows the craniospinal tissue was pulsating much more when the patient was recumbent than upright.

Figure 8A:
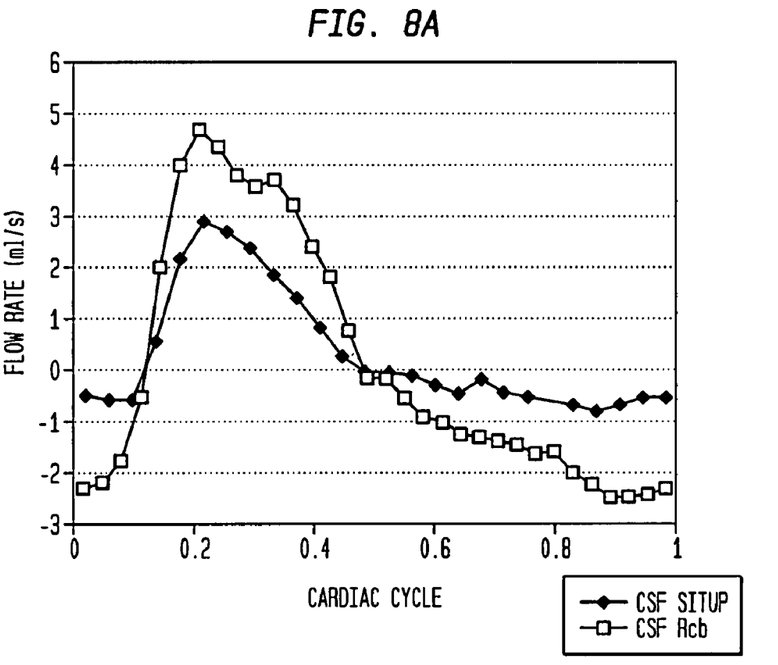
FIGS. 8A and 8B are plots of the cerebrospinal fluid (CSF) flow and spinal cord pulsation respectively with reference to the cardiac cycle.
Figure 8B:
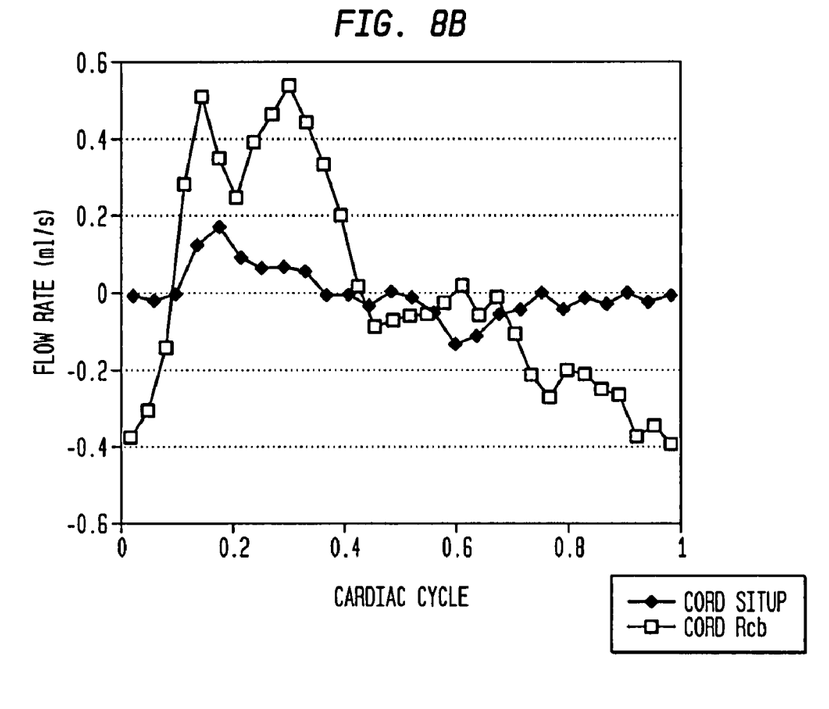

FIGS. 8A and 8B show plots of CSF flow measurements and spinal cord pulsation. These plots show CSF flow was reduced in the upright position 810 as compared to the recumbent position 820. In addition, the patient's spinal cord was moving more in the recumbent position. Table 1 below illustrates flow measurements of CSF through the spinal canal at mid-C2 level from Cine Phase-Contrast MRI. It also illustrates upright imaging reveals changes in flow characteristics that can be used to improve diagnosis and treatment of Chiari malformations.

TABLE 1

|  | Recumbent | Neutral Sit |
| --- | --- | --- |
| Oscillatory part of CSF flow over one cardiac cycle | 0.87 ml | 0.21 ml |
| Net CSF outflow from the brain over one cardiac cycle | −0.06 ml | 0.22 ml |
| Peak systolic flow rate | 4.67 ml/s | 2.88 ml/s |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for detecting chiari malformations, comprising:
   providing a patient-receiving apparatus for positioning a patient in an upright orientation in a patient-receiving space of a magnetic resonance imaging apparatus;
   acquiring magnetic resonance signals of cranio-spinal tissue of the patient in the upright orientation;
   measuring flow of cerebrospinal fluid of the patient in the upright orientation;
   rotating the patient-receiving apparatus so that the patient is positioned in a recumbent orientation in the patient-receiving space of the magnetic resonance imaging apparatus;
   acquiring magnetic resonance signals of the patient's cranio-spinal tissue in the recumbent orientation; and
   processing the magnetic resonance signals acquired in the upright and recumbent orientations to display one or more images that are used to detect the presence or absence of chiari malformations.

2. The method of claim 1, further comprising measuring the flow of the cerebrospinal fluid of the patient in the recumbent orientation.

3. The method of claim 2, further comprising processing the measurement of the cerebrospinal fluid flow to produce an image of the cerebrospinal flow with respect to a cardiac cycle of the patient.

4. The method of claim 1, further comprising processing the magnetic resonance signals acquired in one or more of the recumbent and upright orientations to produce an image of a head of the patient in the recumbent orientation.

5. The method of claim 1, further comprising processing the magnetic resonance signals acquired in one or more of the recumbent and upright orientations to produce an image of a head of the patient in the upright orientation.

6. The method of claim 5, wherein processing further comprises processing the magnetic resonance signals to produce an image of the head of the patient along a coronal plane in the recumbent and upright orientations.

7. The method of claim 1, wherein processing further comprises processing the magnetic resonance signals of one or more of the recumbent and upright orientations to produce an image of a head of the patient along a sagittal plane in the recumbent and upright orientations.

8. The method of claim 1, wherein processing further comprises processing the magnetic resonance signals to produce an image of a head of the patient along a transverse plane in the recumbent and upright orientations.

9. The method of claim 1, wherein providing a patient-receiving apparatus for positioning the patient in the upright orientation comprises positioning the patient in a standing position.

10. The method of claim 1, wherein providing the patient-receiving apparatus for positioning the patient in the upright orientation comprises positioning the patient in a sitting position.

11. A magnetic resonance imaging method, comprising:
    operating a magnetic resonance imaging system to acquire magnetic resonance signals from a head of a patient positioned on a patient support in a recumbent orientation;
    rotating the patient support to place the patient in an upright orientation;
    acquiring by the magnetic resonance imaging system magnetic resonance signals from the head of the patient in the upright orientation; and
    processing the magnetic resonance signals acquired in the upright and recumbent orientation to produce an image of a portion of the patient's head in the recumbent and upright orientation so that the image indicates the presence or absence of a chiari malformation.

12. The method of claim 11, wherein the step of acquiring magnetic resonance image signals is triggered based on a cardiac cycle of the patient.

13. The method of claim 12, further comprising obtaining one or more measurements of cerebrospinal fluid flow of the patient based on the cardiac cycle of the patient.

14. The method of claim 13, further comprising processing the measurements of the cerebrospinal flow to produce an image of the cerebrospinal flow of the patient in the upright and recumbent orientations.

15. The method of claim 11, wherein the signals from the head of the patient further comprise signals from a craniospinal region.

16. A method for detecting chiari malformations, comprising:
    providing a patient-receiving apparatus capable of supporting a patient in an upright orientation in a patient-receiving space of a magnetic resonance imaging apparatus;
    acquiring magnetic resonance signals of cranio-spinal tissue of the patient in the upright orientation;
    constructing images based on the acquired magnetic resonance signals in the sagittal, axial or coronal planes to visualize the cerebellum and brain stem; and
    analyzing the images to detect the presence or absence of chiari malformations.

* * * * *

UNITED STATES PATENT AND TRADEMARK OFFICE
CERTIFICATE OF CORRECTION

| | | |
|---|---|---|
| PATENT NO. | : 8,401,612 B1 | Page 1 of 1 |
| APPLICATION NO. | : 11/900656 | |
| DATED | : March 19, 2013 | |
| INVENTOR(S) | : Ki-Cheung Chu, Raymond V. Damadian and Daniel Culver | |

It is certified that error appears in the above-identified patent and that said Letters Patent is hereby corrected as shown below:

In the Specification
Column 2, line 31, "weight bearing" should read -- weight-bearing --.
Column 2, line 34, "gravity bearing" should read -- gravity-bearing --.
Column 3, line 36, "patient receiving" should read -- patient-receiving --.
Column 3, line 38, "patient receiving" should read -- patient-receiving --.
Column 3, line 47, "position" should read -- positions --.
Column 3, line 47, "so that show" should read -- so that they show --.
Column 3, line 63, "showing cross-sectional" should read -- showing a cross-sectional --.
Column 4, line 29, "their" should read -- "his or her" --.
Column 5, line 35, "upright position" should read -- upright positions --.
Column 5, line 47, "only, is in a" should read -- only is in a --.
Column 6, line 26, "flux generating" should read -- flux-generating --.
Column 6, line 61, "flux generating" should read -- flux-generating --.
Column 7, line 51, "includes processor" should read -- includes a processor --.
Column 7, line 51, "control" should read -- controls --.
Column 7, line 57, "variety positions" should read -- variety of positions --.
Column 8, line 9, "Unix based" should read -- Unix-based --.
Column 8, line 25, "and" should read -- an --.
Column 8, line 29, "shows" should read -- show --.
Column 8, line 50, "shows" should read -- show --.
Column 8, line 61, "are" should read -- is --.

In the Claims
Column 9, line 32, Claim 1, "chiari malformations" should read -- Chiari malformations --.
Column 9, line 50, Claim 1, "chiari malformations" should read -- Chiari malformations --.
Column 10, line 35, Claim 11, "orientation" should read -- Orientations --.
Column 10, line 36, Claim 11, "chiari malformation" should read -- Chiari malformation --.
Column 10, line 50, Claim 16, "chiari malformation" should read -- Chiari malformation --.
Column 10, line 62, Claim 16, "chiari malformation" should read -- Chiari malformation --.

Signed and Sealed this
Seventh Day of July, 2015

Michelle K. Lee
*Director of the United States Patent and Trademark Office*